(12) United States Patent
Heilek et al.

(10) Patent No.: US 8,106,240 B2
(45) Date of Patent: *Jan. 31, 2012

(54) PROCESS FOR OPERATING A CONTINUOUS REMOVAL OF A TARGET PRODUCT X IN THE FORM OF FINE CRYSTALS OF THE TARGET PRODUCT X

(75) Inventors: Joerg Heilek, Bammental (DE); Ulrich Hammon, Mannheim (DE); Klaus Joachim Mueller-Engel, Stutensee (DE)

(73) Assignee: BASF SE, Ludwigshafen (DE)

( * ) Notice: Subject to any disclaimer, the term of this patent is extended or adjusted under 35 U.S.C. 154(b) by 536 days.

This patent is subject to a terminal disclaimer.

(21) Appl. No.: 12/208,559

(22) Filed: Sep. 11, 2008

(65) Prior Publication Data

US 2009/0076232 A1 Mar. 19, 2009

Related U.S. Application Data

(60) Provisional application No. 60/972,023, filed on Sep. 13, 2007.

(30) Foreign Application Priority Data

Sep. 13, 2007 (DE) .......................... 10 2007 043 758

(51) Int. Cl.
*C07C 51/42* (2006.01)
(52) U.S. Cl. ........................................................ 562/600
(58) Field of Classification Search .................. None
See application file for complete search history.

(56) References Cited

U.S. PATENT DOCUMENTS

| | | | |
|---|---|---|---|
| 6,939,991 B2 | 9/2005 | Thiel et al. | |
| 7,112,695 B2 | 9/2006 | Eck et al. | |
| 7,279,075 B2 | 10/2007 | Thiel et al. | |
| 7,393,436 B2 | 7/2008 | Eck et al. | |
| 2005/0090628 A1* | 4/2005 | Eck et al. | ........................ 526/67 |
| 2006/0199976 A1 | 9/2006 | Heilek et al. | |
| 2008/0183014 A1* | 7/2008 | Diefenbacher et al. | ....... 562/600 |

FOREIGN PATENT DOCUMENTS

| | | |
|---|---|---|
| DE | 103 32 758 A1 | 5/2004 |
| DE | 103 00 816 A1 | 7/2004 |
| DE | 10 2005 009 890 A1 | 9/2006 |
| DE | 10 2007 004 960 A1 | 7/2008 |
| WO | WO 01/77056 A1 | 10/2001 |
| WO | WO 2004/035514 A1 | 4/2004 |

OTHER PUBLICATIONS

"Crystallization and Precipitation" in Ullmann's Encyclopedia of Industrial Chemistry, 2005 Wiley-VCH Verlag GmbH & Co. KGaA, Weinheim, pp. 1-51.*
"Kristallisator mit Wärmeübertragungselementen", Research Disclosure Database No. 496005, Aug. 2005, 6 pages.
"Kristallisator mit Wärmeübertragungselementen", Research Disclosure Database No. 479008, 7 pages, 2005.

* cited by examiner

*Primary Examiner* — Karl J Puttlitz
(74) *Attorney, Agent, or Firm* — Oblon, Spivak, McClelland, Maier & Neustadt, L.L.P.

(57) ABSTRACT

A process for operating a continuous removal of a target product X in the form of fine crystals of a liquid phase P comprising the target product X and constituents other than the target product X by cooling suspension crystallization in the secondary chamber of an indirect heat exchanger to which liquid phase P flows continuously with simultaneous continuous flow through the primary chamber of the indirect heat exchanger with a coolant, and continuous withdrawal of a crystal suspension S having a degree of crystallization Y from the secondary chamber in two operating states I and II, wherein the coolant temperature is lower, the mass flow of liquid phase P is greater and the molar proportion of the constituents other than the target product X in the liquid phase P in operating state II is greater than in operating state I.

30 Claims, No Drawings

PROCESS FOR OPERATING A CONTINUOUS REMOVAL OF A TARGET PRODUCT X IN THE FORM OF FINE CRYSTALS OF THE TARGET PRODUCT X

The present invention relates to a process for operating a continuous removal of a target product X in the form of fine crystals of the target product X from a liquid phase P which consists of the target product X and of constituents $B_i$ other than the target product X and whose total mole fraction of constituents $B_i$ has the value $M_B^{tot}$, with the aid of an indirect heat transferrer which has a secondary chamber and at least one primary chamber, in which the secondary chamber and the at least one primary chamber are each separated spatially from one another by at least one material dividing wall which serves as a surface for transfer of heat out of the secondary chamber into the at least one primary chamber, in which a stream of liquid phase P and, as a constituent thereof, a mass flow $\dot{m}_X$ of target product X are conducted into the secondary chamber of the heat transferrer, while the at least one primary chamber is simultaneously flowed through by at least one fluid cooling medium which is fed to the at least one primary chamber with the temperature $T_K^{in}$ such that fine crystals of the target product X are formed from the liquid phase P in the secondary chamber to leave a liquid residual phase R and are suspended in the remaining liquid residual phase R which, compared to the liquid phase P, comprises the constituents other than the target product X in enriched form and whose content of target product X is at least 70% by weight, to obtain a suspension S having a degree of crystallization Y of fine crystals of the target product X in the liquid residual phase R, and a stream of the suspension S is conducted continuously out of the secondary chamber of the heat transferrer, in different operating states I and II, the at least one fluid cooling medium with the temperature $T_K^{in}(I)$ being fed to the at least one primary chamber and the stream of liquid phase P with a mass flow $\dot{m}_X(I)$ of target product X present in the same stream being fed to the secondary chamber in the operating state I, and the at least one fluid cooling medium with the temperature $T_K^{in}(II)$ being fed to the at least one primary chamber and the stream of liquid phase P with a mass flow $\dot{m}_X(II)$ of target product X present in the same stream being fed to the secondary chamber in operating state II, with the proviso that $\dot{m}_X(II) > \dot{m}_X(I)$ and $T_K^{in}(II) < T_K^{in}(I)$.

Processes for continuously removing a target product X in the form of fine crystals from a liquid phase P comprising the target product X and constituents $B_i$ other than the target product X with the aid of an indirect heat transferrer (cooler or crystallizer) having a secondary chamber and at least one primary chamber are known (cf., for example, DE-A 103 32 758, WO 2004/035514, Research Disclosure Database Number 496005 and 479008, and German application 10 2007 004960.0).

By virtue of the transfer of heat from liquid phase P supplied to the secondary chamber through the material dividing wall (the heat transfer surface) which divides the secondary chamber and the at least one primary chamber into the coolant flowing in the at least one primary chamber, the liquid phase P cools until the saturation limit of liquid phase P with target product X is exceeded and oversaturation is counteracted by formation of crystals of the target product X.

The term "degree of crystallization Y" of the crystal suspension S comprising fine target product crystals suspended in the liquid residual phase R in this document means the mass fraction or else proportion by mass of the fine crystals present in the suspension S in the total mass of the suspension S. The degree of crystallization Y is thus calculated as the fraction of the crystal mass $m_{Kr,Y}$ present in the suspension S at the degree of crystallization Y divided by the total mass $m_S$ of the suspension:

$$Y = \frac{m_{Kr,Y}}{m_S}.$$

The degree of crystallization Y of the suspension S is thus necessarily between 0 and 1. The value "0" would correspond to an exclusively liquid phase, and the value 1 would correspond to an exclusively solid phase (i.e., in both cases, a suspension would no longer be present).

When one constituent $B_i$ is present in the liquid phase P in the molar amount $n_i$ (the molar amount $n_i$ is calculated from the mass in which the constituent $B_i$ is present in the liquid phase P divided by the molar mass of the constituent $B_i$) and the target product X is present in the liquid phase P in the molar amount $n_X$ (the molar amount $n_X$ is calculated from the mass in which the target product X is present in the liquid phase P divided by the molar mass of the target product X), the mole fraction $M_B^i$ of the constituent $B_i$ present in the liquid phase P is understood to mean the quotient of the number of moles $n_i$ divided by the sum formed from the number of moles $n_X$ and the particular numbers of moles of all constituents other than the target product X present in the liquid phase P. In other words, $$M_B^i = \frac{n_i}{n_x + \sum_{i=1}^{I} n_j},$$

under the assumption that the liquid phase P comprises a total of I constituents $B_i$ other than the target product X and different from one another.

The total mole fraction $M_B^{tot}$ of the constituents $B_i$ other than the target product X present in the liquid phase P is understood in this document to mean the sum of all individual values $M_B^i$ calculated for the particular constituents $B_i$.

In a corresponding manner, the mole fraction $M_X$ with which the target product X is present in the liquid phase P is defined as $$M_x = \frac{n_x}{n_x + \sum_{i=1}^{I} n_i}.$$

The relationship $M_X + M_B^{tot} = 1$ applies.

A crystallizative removal of a target product X from a liquid phase P comprising the target product X and constituents other than the target product X is employed especially in order to remove the target product X from by-products formed in the course of its preparation. The target product X may already have been prepared directly by chemical reaction in the liquid phase.

Of course, the target product X may also have been prepared, for example, in the gas phase, from which the target product X is subsequently converted to the liquid phase, generally by condensative and/or absorptive measures, normally together with some secondary components which accompany the target product X in the gas phase.

The crystallizative removal of the target product X can now be effected as a "sharp" thermal separating process, in principle directly from the liquid phase which is obtained as described in the course of preparation of target product X and comprises the target product X and secondary components.

Frequently, however, the aforementioned liquid phase, before the use of a crystallizative removal of the target product X, will first be subjected to at least one "nonsharp" thermal separating process for the purpose of removing a portion of the aforementioned secondary components from the target product X.

A nonsharp separating process is defined as a separating process in which, from a thermodynamic point of view, the composition of the phase which forms when the separating process is employed and comprises target product X in enriched form is markedly dependent, in a thermodynamically necessary manner, on the composition of the mixture to be subjected to the separating process (cf., for example, McCabe-Thiele diagram). The nonsharp thermal separating processes include, for example, simple distillation, rectification, absorption, fractional condensation, desorption, extraction, stripping, azeotropic rectification, etc.

In contrast, crystallizative removal is a sharp thermal separating process in that the composition of the crystals which form, from a thermodynamic point of view, is very substantially independent of the composition of liquid starting mixture (see also DE-A 10 2005 009 890 and DE-A 103 00 816).

The reason for the advantage of the nonsharp separating processes is generally that they can be operated with high space-time yield. A disadvantage of nonsharp separating processes is, however, that the separating action achieved with them is comparatively restricted.

A disadvantage of sharp separating processes is their normally comparatively limited space-time yield, but normally with very high separating action.

Against the above background, the two separating principles are therefore frequently also employed in the following combination.

First, at least one nonsharp thermal separating process is applied to the product mixture obtained in the course of preparation of the target product X to obtain liquid phase P which already comprises the target product X, compared to its proportion by weight in the product mixture, in enriched form. This liquid phase P which, as well as the target product X, still comprises secondary components other than the target product X is subsequently subjected to a crystallizative removal of the target product X, and the liquid residual phase R which remains (which is frequently also referred to as mother liquor), which comprises the secondary components in comparatively enriched form, is recycled at least partly into at least one of the nonsharp thermal separating processes employed beforehand. In this way, the advantages of the two separating principles can be brought to bear simultaneously.

In many cases, a liquid phase P which comprises a target product X and is to be subjected to a crystallizative removal of the target product X (and this also applies to the liquid phases P relevant in this application) therefore comprises at least two, in many cases at least three or four, frequently at least five or six and often at least seven or eight, or at least nine or ten, secondary components other than the target product X (such secondary components are present in the liquid phase P in the context of this application when they are detectable as a constituent thereof, for example, by gas chromatography, liquid chromatography or other means (for example, such as water by Karl Fischer titration)).

In addition to by-products characteristic of the target product X according to its preparation, the liquid phase P comprising the target product X may also comprise solvent or solvent mixture and/or assistants (e.g. absorbents, extractants, etc.) used additionally in the course of for removal of the target product X from a reaction product mixture in the course of generation of liquid phase P. In other words, the liquid residual phase R may, for example, either be melts of the target product X and impurities or solutions of target product X and solvents (or solvent mixtures), and also generally impurities.

A process as described above for continuous crystallizative removal of a target product X from a liquid phase P comprising the target product X and also secondary components (constituents) other than the target product X is typically followed by a continuous process for removing the crystals of the target product X present suspended in the liquid residual phase R in the (crystal) suspension S from the liquid residual phase R ("the mother liquor").

Such a removal can be undertaken, for example, by filtration, by screen centrifugation and/or in wash columns, as disclosed, for example, by WO 01/77056 and the prior art cited therein. Normally, such a removal also includes a wash of the crystals removed in order to remove mother liquor adhering on the crystal surface. Such a wash can be effected, for example, with the melt of crystals which have been removed and washed beforehand.

What is essential for an efficient (with regard both to the separating action and the space-time yield) continuous removal of the suspension crystals from remaining mother liquor (liquid residual phase R) is that the design of the separating apparatus used for the removal is adjusted to the degree of crystallization Y of the (crystal) suspension S, and Y remains stable within certain limits during the continuous operation. For example, the degree of crystallization Y of the suspension S influences all flow technology properties of the suspension S. However, it also influences, for example, the inner structure of the crystal cake to be washed or of the crystal bed to be washed and, as a result, also partly determines the washing action and the pressures which exist in the course of washing. In particular, the pressures, for example in the case of wash columns with forced transport as the given separating apparatus, in the case of an undesired rise in the degree of crystallization Y with otherwise identical mass flows, may rise steeply (for example exponentially) in unfavorable cases and cause either a safety shutdown or damage to the separating apparatus. The degree of crystallization Y, however, also influences the permeability of the crystal cake or crystal bed for the liquid residual phase R (the mother liquor remaining in the crystallizative removal). Moreover, in the case of small degrees of crystallization Y, when pusher centrifuges are used for crystal removal, there may be overshooting of the crystal suspension. In hydraulic wash columns, excessively low degrees of crystallization Y may cause the loss of the stable crystal bed.

Depending on the particular separating problem (including the separating apparatus used) and the nature and size of the crystal assembly, the ideal degree of crystallization Y is frequently in the range of from 0.10 to 0.50, with greater frequency in the range from 0.20 to 0.40, and it is particularly frequently from 0.25 to 0.35 or 0.30.

In a continuous removal as described at the outset of a target product X in the form of fine crystals of the target product X from a liquid phase P comprising the target product X and constituents other than the target product X using a crystallization process as described at the outset of this document, it is therefore desirable that the degree of crystallization Y on which the design of the apparatus is based is kept constant within certain limits (which are specific for the particular separation problem and the separating system employed in each case) over the operating time of the separating process.

Advantageously, the product of degree of crystallization Y with the number 100, over the operating time of the separating process, should deviate from the corresponding product of the target value desired for Y or of the steady-state value (as a reference basis) of Y by not more than ±30%, better by not more than ±20%, advantageously by not more than ±10%, better by not more than ±5%, preferably by not more than ±4%, more preferably by not more than ±3% and most preferably by not more than ±2% or by not more than ±1%.

In the case of a stream of liquid phase P fed unchanged to the secondary chamber of the heat transferrer and a stream of fluid cooling medium conducted unchanged through the at least one primary chamber over the operating time, the degree of crystallization Y of the (crystal) suspension S conducted continuously out of the secondary chamber is determined especially by the temperature $T_K^{in}$ with which the fluid cooling medium is fed to the at least one primary chamber.

In many cases, for example, the market demand for a target product X (for example for an organic target compound such as acrylic acid, methacrylic acid, p-xylene or N-vinylpyrrolidone) is not a stable parameter but rather fluctuates over prolonged periods. For example, it can rise sharply. Instead of reacting to such a rise in market demand with an additional production plant, it is also possible to react to it with an increase in the space-time yield of target product X in already existing production plants. Conversely, in the event that the market demand for target product X declines again, the space-time yield of target product X in the same production plant must be lowered again.

Such a transition from a steady operating state to another steady operating state, in the case of a crystallizative removal of the target product X from the liquid phase P comprising it as described at the outset of this document, is possible, for example, by raising or lowering the stream of liquid phase P to be fed to the secondary chamber of the heat transferrer according to an increasing or decreasing market demand for target product X, and simultaneously adjusting $T_K^{in}$ such that a crystal stream increased or reduced according to the change in market demand can be conducted out of the secondary chamber of the heat transferrer as a constituent of the suspension S stream.

When the stream of liquid phase P to be fed to the secondary chamber of the heat transferrer is increased, $T_K^{in}$ will normally be reduced and, when the stream of liquid phase P to be fed to the secondary chamber of the heat transferrer is reduced, $T_K^{in}$ will generally be increased again.

A disadvantage in the case of use of a procedure as described above has been found to be that the tendency to form crystallizative encrustations on the side of the at least one dividing wall separating the at least one primary chamber from the secondary chamber in each case which faces the secondary chamber increases with decreasing $T_K^{in}$, as does the ability of the encrustation to remain adhering on the dividing wall. However, the formation of crystal layers which remain adhering on the dividing wall is accompanied by a reduction of the heat transfer through the dividing wall, which counteracts the objective of the crystallizative removal of the target product X. For the above reason, the side of such dividing walls facing the secondary chamber is in many cases operated with wiping. In other words, a wiper apparatus driven within the secondary chamber (for example analogously to the windshield wipers of an automobile) is used to continuously wipe away (continuously scratch off or away) crystals of target product X remaining adhering on the relevant side of the dividing wall, and suspends them in the suspension S. At the same time, the wiper apparatus generally brings about mixing of the crystal suspension S in the secondary chamber.

However, even in the case of wiped dividing walls, a tendency to crystallizative encrustation which increases with decreasing $T_K^{in}$ is found to be disadvantageous in that it is accompanied in each case by increased wear on the comparatively complex wiper apparatus. Furthermore, the wiper performance to be rendered increases and, in the extreme case, the wiper apparatus is no longer able to accomplish the wiping task to be fulfilled, such that remaining encrustations can form, in which the wipers may become stuck. Furthermore, such crystallizative encrustations, once they attain a particular degree, may spontaneously become detached as comparatively voluminous individual pieces and cause consequent damage of a wide variety of different kinds.

For example, they may lead to damage to the pump used to convey the crystal suspension S conducted out of the secondary chamber (for example a centrifugal pump.

In the worst case, the crystallization process has to be stopped and the crystal encrustation formed melted off. In some cases, the wiper apparatus may be damaged in the course of formation of encrustation.

Against this background, it was an object of the present invention to provide a process as described at the outset of this document, which has the disadvantageous consequences detailed above to a reduced degree, if at all.

Accordingly, a process is provided for operating a continuous removal of a target product X in the form of fine crystals of the target product X from a liquid phase P which consists of the target product X and of constituents $B_i$ other than the target product X and whose total mole fraction of constituents $B_i$ has the value $M_B^{tot}$, with the aid of an indirect heat transferrer which has a secondary chamber and at least one primary chamber, in which the secondary chamber and the at least one primary chamber are each separated spatially from one another by at least one material dividing wall which serves as a surface for transfer of heat out of the secondary chamber into the at least one primary chamber, in which a stream of liquid phase P and, as a constituent thereof, a mass flow $\dot{m}_X$ of target product X are conducted into the secondary chamber of the heat transferrer, while the at least one primary chamber is simultaneously flowed through by at least one fluid cooling medium which is fed to the at least one primary chamber with the temperature $T_K^{in}$ such that fine crystals of the target product X are formed from the liquid phase P in the secondary chamber to leave a liquid residual phase R and are suspended in the remaining liquid residual phase R which, compared to the liquid phase P, comprises the constituents other than the target product X in enriched form and whose content of target product X is at least 70% by weight, to obtain a suspension S having a degree of crystallization Y of fine crystals of the target product X in the liquid residual phase R, and a stream of the suspension S is conducted continuously out of the secondary chamber of the heat transferrer, in different operating states I and II, the at least one fluid cooling medium with the temperature $T_K^{in}$ (I) being fed to the at least one primary chamber and the stream of liquid phase P with a mass flow $\dot{m}_X$ (I) of target product X present in the same stream being fed to the secondary chamber in the operating state I, and the at least one fluid cooling medium with the temperature $T_K^{in}$ (II) being fed to the at least one primary chamber and the stream of liquid phase P with a mass flow $\dot{m}_X$ (II) of target product X present in the same stream being fed to the secondary chamber in operating state II, with the proviso that $\dot{m}_X(II) > \dot{m}_X(I)$ and $T_K^{in}(II) < T_K^{in}(I)$, wherein the total mole fraction $M_B^{tot}$ of constituents $B_i$ other than the target product X in the liquid phase P fed to the secondary chamber is greater in operating state II than in operating state I.

In other words, the approach to a solution of the present invention, in order to counteract the increased encrustation tendency accompanying decreasing $T_K^{in}$ with simultaneously increased $\dot{m}_X$ under otherwise essentially unchanged operating conditions on the side of the at least one dividing wall separating the at least one primary chamber from the secondary chamber in each case which faces the secondary chamber, consists in increasing the total mole fraction of constituents $B_i$ other than the target product X (i.e. $M_B^{tot}$) in the liquid phase P fed to the secondary chamber in a controlled manner.

Ultimately, this approach derives from the fact that the greater $M_B^{tot}$ in the liquid phase P is, the lower is that temperature of a liquid phase P comprising the target product X at which crystals of the target product X present dissolved therein are formed from this liquid phase (neglecting the possibility of occurrence of oversaturation phenomena). In the literature, this phenomenon is also referred to as molar "crystallization point depression".

In this context, the connection to the increasing/decreasing encrustation tendency presumably arises as follows.

Normally, in an indirect heat transferrer, the at least one dividing wall between the secondary chamber and the at least one primary chamber has a comparatively high thermal conductivity, such that the temperature on the side of such a dividing wall facing the secondary chamber is not very far away from that temperature that the fluid cooling medium flowing through the primary chamber has. At the same time, an interface layer composed of liquid phase P comprising the target product X and the constituents $B_i$ other than the target product X is normally present on the side of such a dividing wall facing the secondary chamber.

When crystals form (there is "layer crystallization") in this interface layer, the crystals which originate from the individual crystallization nuclei grow onto one another until the total mole fraction of the constituents $B_i$ present in the mother liquor remaining in liquid form in the interface layer has become so great that the temperature existing in the interface layer is no longer capable of causing any further deposition.

When the total mole fraction of constituents $B_i$ present in the interface layer already present before formation of crystals in the interface layer is comparatively high, the crystal growth under the same temperature boundary conditions ends at a relatively early stage, at a time at which the proportion by weight of the mother liquor remaining in liquid form in the interface layer is still comparatively high at the interface layer. However, these constituents remaining in liquid form disrupt both the cohesion between the different crystals and their adhesion on the side of the dividing surface between secondary chamber and the at least one primary chamber facing the secondary chamber. Both of the above effects reduce the formation of crystal encrustations on the side of the aforementioned separating surface facing the secondary chamber (when, in contrast, the total mole fraction of constituents $B_i$ in the interface layer before the formation of crystals is low, the crystal growth, under the same temperature boundary conditions, does not end until a time where the proportion by weight of mother liquor remaining in liquid form is only small; the latter promotes the encrustation tendency). Expressed in other words, an increased total mole fraction of constituents $B_i$ other than the target product X present in the liquid phase P, even at a comparatively low $T_K^{in}$, still ensures that a perceptible proportion of liquid mother liquor remains in the interface layer, and thus reduces the encrustation tendency in question.

In this context, it is surprising and essential to the invention that an increase of $M_B^{tot}$ in the liquid phase P causes an additional lowering of that temperature at which crystal formation in the liquid phase P sets in, but the encrustation tendency at this lower crystal formation temperature is nevertheless less marked than in the case of a crystal formation temperature corresponding to a lower $M_B^{tot}$. Among other reasons, this situation is presumably also attributable to the fact that, in the case of the increased $M_B^{tot}$ in the liquid phase P, the crystal formation is accompanied by the formation of an increased number of crystal nuclei.

The difference between $\dot{m}_X$ (I) and $\dot{m}_X$ (II) may, based on the arithmetic mean of the two mass flows, in the process according to the invention, be at least 5%, or at least 10%, or at least 15%, or at least 20%, or at least 30%, or at least 40%, or at least 50%, or at least 60%, or at least 70%, or at least 80%, or at least 90%, or at least 100% or more. In general, the difference on the same basis will, however, not be more than 190%, usually not more than 180% and frequently not more than 170%.

The difference between $T_K^{in}$ (II) and $T_K^{in}$ (I) is normally configured such that, with the same flow of the coolant stream flowing through the at least one primary chamber, the degree of crystallization Y (II) of the crystal suspension S withdrawn from the secondary chamber in operating state II and the degree of crystallization Y (I) of the crystal suspension S withdrawn from the secondary chamber in operating state I, based on the arithmetic mean of Y (I) and Y (II), differ from one another by not more than 20%, advantageously by not more than 10%, preferably by not more than 5%, more preferably by not more than 3% and more preferably by not more than 1%.

In many cases, the difference between $T_K^{in}$ (II) and $T_K^{in}$ (I) will be up to 30 K or more. Frequently, the difference between $T_K^{in}$ (II) and $T_K^{in}$ (I) will also be only up to 25 K, or only up to 20 K, or only up to 15 K, or only up to 10 K, or only up to 5 K. Of course, the process according to the invention is also suitable when the difference between $T_K^{in}$ (II) and $T_K^{in}$ (I) is only from 0.1 to 5 K, or only from 0.2 to 4 K, or only from 0.3 to 3 K, or only from 0.4 or 0.5 to 2 K, or from 0.7 to 2 K, or from 0.9 or 1 to 2 K. Often, the difference between $T_K^{in}$ (II) and $T_K^{in}$ (I) will be at least 0.1 K or at least 0.2 K, or at least 0.3 K.

To increase the total mole fraction $M_B^{tot}$ to the value desired in the operating state II, in principle, any of the constituents (constituent types) $B_i$ present therein as a result of the preparation can be added to the liquid phase P comprising the target product X. In principle, to increase the total mole fraction $M_B^{tot}$ to the value desired in operating state II, it is, though, also possible to add those constituents which would not have been present in the liquid phase P as a result of the preparation. It will be appreciated that $M_B^{tot}$ in the liquid phase P can, though, also be increased by adding both of the above types of constituents other than the target product X.

Advantageously in accordance with the invention, the total number of moles of constituents $B_i$ which are present in the liquid phase P (II), which are different than the target product X and whose molecular weight is less than three times (preferably less than twice) the molecular weight of the target product X (preferably less than the molecular weight of the target product X) present in the liquid phase P (the liquid phase P(II)) fed to the secondary chamber in operating state II is greater than the total number of moles of constituents $B_i$ which are present in the liquid phase P (I), which are different than the target product X and whose molecular weight is less than three times (preferably less than twice) the molecular weight of the target product X (preferably less than the molecular weight of the target product X) present in the liquid phase P (the liquid phase P (I)) fed to the secondary chamber in operating state I. The total number of moles is the sum of all numbers of moles $n_i$ of the constituents $B_i$ present in each case in the liquid phase P, provided that the molecular weight of the constituents $B_i$ taken into account in forming the sum is less than three times the molecular weight (or twice the molecular weight or the molecular weight) of the target product X.

In other words, advantageously in accordance with the invention, the total mole fraction $M_B^{tot}$ is increased to its value in operating state II (also referred to in this document as $M_B^{tot}$ (II)), starting from its value in operating state I (also referred to in this document as $M_B^{tot}$ (I)) by also using (or exclusively using) those constituents $B_i$ whose molecular weight is less than twice the molecular weight of the target product X and preferably less than the molecular weight of the target product X (conditions 1). Normally, both the target product X and the constituents $B_i$ of liquid phase P other than the target product X are present dissolved in the liquid phase P.

Preferably in accordance with the invention, the total mole fraction $M_B^{tot}$ is increased to its value in operating state II (starting from its value in operating state I), in addition, by also using (or exclusively using) those constituents $B_i$ whose depletion coefficient $A^{Bi}$ in the course of the (inventive) continuous crystallizative removal of the target product X, is at least $\geq 5$, more preferably $\geq 10$ and even better $\geq 15$ (conditions 2). The depletion coefficient $A^{Bi}$ is understood to mean the concentration ratio of concentration of constituent $B_i$ remaining in the mother liquor to concentration of constituent $B_i$ remaining in the crystals (in each case expressed as % by weight based on the total amount of remaining mother liquor (or liquid residual phase R) or the total amount of crystals formed). A removal of crystals/mother liquor to an extent of more than 90% by weight, preferably to an extent of more than 95% by weight, or 97, 98 or 99% by weight, of the total amount of mother liquor is generally sufficient to determine $A^{Bi}$ (the influence of the residual moisture on the crystals is generally negligible). The aforementioned values of $A^{Bi}$ are preferably based on the combination of suspension crystallization and subsequent removal of the suspension crystals formed from the suspension S which is employed in the course of preparation of target product X.

Particular preference is given in accordance with the invention to increasing the total mole fraction $M_B^{tot}$ to its value in operating state II (starting from its value in operating state I) by also using (or exclusively using) those constituents $B_i$ which satisfy both condition 1 and condition 2.

Very particular preference is given in accordance with the invention to increasing the total mole fraction $M_B^{tot}$ to its value in operating state II (starting from its value in operating state I) by also using (or exclusively using) those constituents $B_i$ which satisfy both a preferred condition 1 and a preferred condition 2.

Particularly advantageously, the above constituents $B_i$ are those which, in terms of their type, are present in any case in the liquid phase P as a result of the preparation.

In general, the increase of $M_B^{tot}$ to its value for the operating state II is effected only to the extent as required from an application point of view for reasons of reduction in encrustation, since the increase of $M_B^{tot}$ in the liquid phase P fed to the secondary chamber in the removal of the target product X from the liquid phase P is accompanied by an increased separation complexity.

In general, the increase from $M_B^{tot}$ (I) to $M_B^{tot}$ (II) in the process according to the invention is effected at least to such a degree that the crystal formation onset temperature of the liquid phase P (II) is at least 0.1 K, often at least 0.2 K and frequently at least 0.3 K below the crystal formation onset temperature of the liquid phase P (I). The crystal formation onset temperature of a liquid phase P is understood to mean that temperature which is present in the liquid phase P at the moment which is reached when, proceeding from a crystal suspension S obtained from the liquid phase P by cooling it, heat is supplied to this crystal suspension S with constant (in the ideal case ideal) mixing, in order to melt the crystals present in the crystal suspension S, and the last crystal has just melted. In some cases, it is also referred to in the literature as the dissolution temperature.

Frequently, the increase from $M_B^{tot}$(I) to $M_B^{tot}$(II) in the process according to the invention is effected to such an extent that the crystal formation onset temperature of the liquid phase P (II) is up to 30 K (or up to 20 K, or up to 15 K, or up to 10 K, or up to 5 K, or up to 4 K, or up to 3 K, or up to 2 K, or up to 1 K, or up to 0.5 K) below the crystal formation onset temperature of the liquid phase P (I).

Appropriately in application terms, the increase from $M_B^{tot}$ (I) to $M_B^{tot}$ (II) in the liquid phase P can be undertaken in a simple manner by adding (mixing in) the additional constituents $B_i$ contemplated to the desired degree to a separately obtained liquid phase P before it is fed into the secondary chamber of the indirect heat transferrer. Among other reasons, such a procedure is advantageous in that, at the transition from an operating state (II) to an operating state (I), the added amounts of additional constituents $B_i$ are simply omitted again (or reduced when the new operating state (I) is different than the original operating state (I)). Preferably, at the transition from an operating state I to an operating II, the procedure will be to initially retain all boundary conditions of the operating state I and to increase only $M_B^{tot}$ to the desired degree. Subsequently, $T_K^{in}$ will be lowered to the extent that the crystallization temperature in the substance mixture present in the secondary chamber declines, in order to essentially maintain Y. Thereafter, $\dot{m}_X$ is increased from $\dot{m}_X$ (I) to $\dot{m}_X$ (II) (by correspondingly increasing the current of the liquid phase P fed to the secondary chamber) and, accompanying this, $T_K^{in}$ is lowered further for the purpose of substantially maintaining Y. At the transition from an operating state II to an operating state I, the process can essentially be reversed.

In other words, $\dot{m}_X$ (II) will first be lowered again to $\dot{m}_X$ (I) and, accompanying this, $T_K^{in}$ will be increased again in order to substantially maintain Y. Thereafter, $M_B^{tot}$(II) will be lowered to $M_B^{tot}$ (I), and then $T_K^{in}$ will be increased further to the extent to which the crystallization temperature increases again in the substance mixture present in the secondary chamber until the desired operating state (I) is attained.

In other words, at the transition from an operating state I to an operating state II, the increase from $M_B^{tot}$ (I) to $M_B^{tot}$ (II) is advantageously effected before the increase from $\dot{m}_X$(I) to $\dot{m}_X$(II). In contrast, at the transition from an operating state II to an operating state I, the lowering from $\dot{m}_X$ (II) to $\dot{m}_X$ (I) is effected before the lowering from $M_B^{tot}$ (II) to $M_B^{tot}$ (I).

At the transition from an operating state II to an operating state I, a lowering from $M_B^{tot}$ (II) to $M_B^{tot}$ (I) is also advantageous in that, at a lower $M_B^{tot}$, the crystals of the target product X removed in accordance with the invention have a coarser granularity, which normally eases the subsequent separation of crystals and remaining liquid residual phase R. A lower value for $M_B^{tot}$ is also found to be advantageous in the case of separation of crystals and remaining liquid residual phase R with the aid of a pure melt wash column with forced transport of the crystal bed by virtue of the fact that it reduces the temperature difference between the liquid residual phase R and the pure melt (melt of crystals of target product X removed beforehand), which limits the recrystallization of target product X from the pure melt used to wash the crystal bed, and thus ensures an appropriate permeability of the crystal bed for liquid phase ("wash melt").

A low value of $M_B^{tot}$ is also advantageous from the aspect that the liquid residual phase R which is removed from the crystals and still comprises target product X, to reduce losses of target product X, is normally recycled into a nonsharp separating process also used in many cases in the course of preparation of liquid phases P (cf., for example FIG. 5 of WO 01/77056). When the liquid residual phase R thus recycled comprises a lower proportion of constituents other than the target product X, this reduces the separation complexity in the nonsharp separation stage.

It will be appreciated that the change in $M_B^{tot}$ in the liquid phase P can also be undertaken integrated directly within the process for preparing the liquid phase P. This can be done, for example, by correspondingly varying the number of theoretical plates on the route to the liquid phase P. The latter can be done, for example, in a simple manner by varying the reflux ratio in a separating column.

In principle, in the process according to the invention, both the operating state II and the operating state I may be the operating state existing earlier in time.

The process according to the invention is suitable when the content in the liquid residual phase R (mother liquor) present in the suspension S withdrawn from the secondary chamber of target product X in the two operating states I, II is >70% by weight. However, it is also suitable when the aforementioned content of target product X in the liquid residual phase R in the two operating states I,II is $\geq$75% by weight, or $\geq$80% by weight, or $\geq$85% by weight, or $\geq$87% by weight, or $\geq$90% by weight, or $\geq$92% by weight, or $\geq$94% by weight, or $\geq$95% by weight, or $\geq$96% by weight, or $\geq$98% by weight, or $\geq$99% by weight. In general, the aforementioned content of target product X in the two operating states I,II will, however, be $\leq$99.95% by weight, usually $\leq$99.9% by weight.

In other words, the process according to the invention is suitable in the case of those liquid phases P whose content of target product X in the two operating states I,II is >70% by weight, $\geq$75% by weight, or $\geq$80% by weight, or $\geq$85% by weight, or $\geq$87% by weight, or $\geq$90% by weight, or $\geq$92% by weight, or $\geq$94% by weight, or $\geq$95% by weight, or $\geq$96% by weight, or $\geq$98% by weight, or $\geq$99% by weight. In general, the aforementioned content in the liquid phase P fed in the process according to the invention to the secondary chamber of the heat transferrer of target product X in the two operating states I,II will, however, be $\leq$99.995% by weight, usually $\leq$99.99% by weight.

The temperature with which the at least one fluid cooling medium is fed in the process according to the invention to the at least one primary chamber of the heat transferrer ($T_K^{in}$), is necessarily below that temperature with which the liquid phase P is simultaneously fed to the secondary chamber of the heat transferrer. Moreover, $T_K^{in}$ is necessarily below the crystallization onset temperature.

Useful target products X for the suspension crystallization conducted as a cooling crystallization in accordance with the invention include, for example, saturated or unsaturated carboxylic acids such as acetic acid, propionic acid, acrylic acid and methacrylic acid, or substituted aromatics (with, for example, halogens, methyl, carboxyl, hydroxyl and/or nitrogen groups (e.g. —$NH_2$) as substituents), such as p-xylene, cresol and chlorobenzene, or polycyclic aromatic compounds such as naphthalene and bisphenol A, or isocyanates such as TDI and MDI, or vinyl compounds such as N-vinylpyrrolidone, or formaldehyde oligomers such as trioxane, or inorganic salts such as sodium or potassium salts (e.g. the sulfates, chlorides, bromides and iodides).

In particular, the process according to the invention is suitable in the case of acrylic acid, methacrylic acid, p-xylene or N-vinylpyrrolidone as the target product X, since a significant proportion of the by-products obtained in the course of their preparation has a lower molecular weight than the particular target product X itself.

When acrylic acid is the target product X, for example, water, diacrylic acid (Michael adduct), methacrylic acid, benzoic acid, formic acid, acetic acid and propionic acid are constituents $B_i$ which are suitable in accordance with the invention and can be added in a controlled manner to the liquid phase P comprising the target product X (in this case the acrylic acid), in order to increase its $M_B^{tot}$.

Particularly advantageously in accordance with the invention, in the case of acrylic acid as the target product X, $M_B^{tot}$ in the liquid phase P is varied by using (adding to the liquid phase P as required) so-called acid water, as is normally obtained in the course of removal of acrylic acid from the product gas mixture of a heterogeneously catalyzed partial gas phase oxidation of a $C_3$ precursor compound of acrylic acid (e.g. propane, propylene, acrolein, propionic acid, propanol, glycerol and/or propionaldehyde) (cf., for example, WO 2004/035514, German application 10 2007 004 960.0, DE-A 102 43 625 and DE-A 103 23 758). In general, acid water comprises at least 60% by weight (frequently at least 70% by weight, usually at least 75% by weight, in many cases at least 80% by weight) of water and at least 3% by weight (frequently at least 5% by weight, often at least 7% by weight, in many cases at least 9% by weight or at least 11% by weight) of acrylic acid.

In addition, acid water comprises small amounts of other carboxylic acid by-products formed in the course of the heterogeneously catalyzed partial gas phase oxidation of the $C_3$ precursor compound to acrylic acid, such as acetic acid, propionic acid and formic acid. Use of acid water for the inventive regulation of $M_B^{tot}$ in the liquid phase P is found to be advantageous especially when an arrangement as in FIG. 5 of WO 01/77056 is employed in the acrylic acid preparation (a corresponding arrangement is also described by German application 10 2007 004 960.0). As a result of the use of acid water ("water which comprises acrylic acid and is withdrawn from the process for preparing acrylic acid" (or aqueous solution); such acid water can always be withdrawn from a process for preparing acrylic acid comprising a heterogeneously catalyzed partial gas phase oxidation of a $C_3$ precursor compound of acrylic acid and a subsequent acrylic acid removal from the product gas mixture of the gas phase oxidation, since water is an unavoidable by-product of the heterogeneously catalyzed partial gas phase oxidation; the water content of such an aqueous solution may be at least 60% by weight, or at least 70% by weight, or at least 75% by weight, or at least 80% by weight), it is possible to minimize the acrylic acid losses which occur overall in the process for preparing acrylic acid. Acid water may also have been used at an earlier stage, to adjust $M_B^{tot}$ in the liquid phase P fed to the secondary chamber in operating state I.

When methacrylic acid is the target product X, for example, water, acrylic acid and acetic acid are constituents $B_i$, which are suitable in accordance with the invention and can be added in a controlled manner to the liquid phase P comprising the target product X (in this case the methacrylic acid), in order to increase its $M_B^{tot}$.

When p-xylene is the target product X, for example, water and also m- and o-xylene are constituents $B_i$ which are suitable in accordance with the invention and can be added in a controlled manner to the liquid phase P comprising the target product X (in this case the p-xylene) in order to increase its $M_B^{tot}$.

When N-vinylpyrrolidone (also 1-vinyl-2-pyrrolidone) is the target product X, for example, water and 2-pyrrolidone are constituents $B_i$ which are suitable in accordance with the invention and can be added to the liquid phase comprising the target product X (in this case the N-vinylpyrrolidone), in order to increase its $M_B^{tot}$.

The process according to the invention is very particularly suitable in the case of acrylic acid as the target product X and crude acrylic acid as the liquid phase P, which, in the two operating states I, II, has, for example, one of the following sets of contents:

| | |
|---|---|
| >70% by weight of | acrylic acid, |
| up to 15% by weight | of acetic acid, |
| up to 5% by weight of | propionic acid, |
| up to 5% by weight of | low molecular weight aldehydes, |
| up to 3% by weight of | polymerization inhibitors, |
| 0 to 5% by weight of and | diacrylic acid (Michael adduct), |
| up to 25% by weight of | water; |
| or | |
| ≧80% by weight of | acrylic acid, |
| ≧100 ppm by weight to ≦15% by weight of | acetic acid, |
| ≧10 ppm by weight to ≦5% by weight of | propionic acid, |
| up to 5% by weight of | low molecular weight aldehydes, |
| up to 3% by weight of | polymerization inhibitors and |
| 0 to 5% by weight of and | diacrylic acid (Michael adduct), |
| up to 15% by weight of | water; |
| or | |
| ≧85% by weight of | acrylic acid, |
| ≧100 ppm by weight to ≦10% by weight of | acetic acid, |
| ≧10 ppm by weight to ≦5% by weight of | propionic acid, |
| up to 5% by weight of | low molecular weight aldehydes, |
| up to 3% by weight of | polymerization inhibitors, |
| 0 to 5% by weight of and | diacrylic acid (Michael adduct), |
| up to 10% by weight of | water; |
| or | |
| ≧90% by weight of | acrylic acid, |
| ≧100 ppm by weight to ≦5% by weight of | acetic acid, |
| ≧10 ppm by weight to ≦2% by weight of | propionic acid, |
| up to 2% by weight of | low molecular weight aldehydes, |
| up to 2% by weight of | polymerization inhibitors, |
| 0 to 3% by weight of and | diacrylic acid (Michael adduct), |
| up to 9% by weight of | water; |
| or | |
| ≧95% by weight of | acrylic acid, |
| ≧100 ppm by weight to ≦3% by weight of | acetic acid, |
| ≧10 ppm by weight to ≦2% by weight of | propionic acid, |
| up to 2% by weight of | low molecular weight aldehydes, |
| up to 2% by weight of | polymerization inhibitors, |
| 0 to 2% by weight of and | diacrylic acid (Michael adduct), |
| up to 4.9% by weight of | water; |
| or | |
| 93 to 98% by weight of | acrylic acid, |
| 1 to 5% by weight of | water, |
| 0.001 to 3% by weight of | acrolein, |
| ≧0 to 3% by weight of | methacrolein, |
| ≧0 to 3% by weight of | methacrylic acid, |
| 0.1 to 3% by weight of | acetic acid, |
| 0.01 to 3% by weight of | propionic acid, |
| 0.001 to 3% by weight of | formaldehyde, |
| 0.001 to 3% by weight of | aldehydes other than formaldehyde, |
| 0.01 to 3% by weight of | maleic acid, and |
| ≧0 to 3% by weight of | protoanemonin. |

Crude acrylic acids are obtainable, for example, by the known prior art processes (cf., for example, WO 01/77056, DE-A 103 32 758, DE-A 102 43 625, German application 10 2006 057 631.4, German application 10 2006 062 258.8, German application 10 2007 004 960.0, WO 2004/035514, German application 10 2006 049 939.5, DE-A 10 2005 029 629, WO 03/041832 and DE-A 10 2005 015 639 and also the prior art cited in these documents).

These are generally crude acrylic acids which are obtained (derived) from the product gas mixture of a heterogeneously catalyzed partial oxidation of at least one $C_3$ precursor compound of acrylic acid (e.g. propane, propylene, glycerol, acrolein, propionic acid, propanol and/or propionaldehyde).

For the process according to the invention, a useful crude acrylic acid for obtaining the liquid phases P in the two operating states I, II is especially one which has been obtained from the product gas mixture of a heterogeneously catalyzed partial gas phase oxidation of at least one $C_3$ precursor compound using at least one nonsharp separating process. This is especially true when the acrylic acid crystals present suspended in the liquid residual phase R in the suspension S obtained when the process according to the invention is applied to such a liquid phase P are subsequently removed from the liquid residual phase R, and the remaining residual phase R is recycled at least partly into at least one of the nonsharp separating processes used to prepare the crude acrylic acid from the product gas mixture of the gas phase partial oxidation.

As already mentioned, acid water is the preferred additive in these cases for the inventive adjustment of $M_B^{tot}$ in the liquid phase P.

The basic structure of such a combined use of nonsharp separating processes and the sharp separating process of crystallization is taught, for example, by DE-A 196 06 877, EP-A 792 867, and also EP-A 1 484 308, EP-A 1 116 709 and especially EP-A 1 015 410.

In general, the at least one nonsharp separating process also employed to obtain the liquid phase P to be treated in accordance with the invention from the product gas mixture of a heterogeneously catalyzed partial gas phase oxidation of at least one $C_3$ precursor compound of acrylic acid will be a distillation, rectification, absorption, adsorption, extraction, desorption, stripping, distraction, (partial) condensation, fractional condensation, a membrane separating process such as a pervaporation/vapor permeation, or a combination of such processes.

In the simplest case, the crude acrylic acid to be used to obtain the liquid phase P may be the absorbate and/or partial condensate and/or condensate obtained by fractionation from an absorptive and/or condensative removal of acrylic acid from the product gas mixture of a heterogeneously catalyzed partial gas phase oxidation of at least one of the $C_3$ precursors listed in this document. The liquid residual phase R (mother liquor) removed from the suspension S is then appropriately recycled into the absorption and/or condensation (cf., for example, EP-A 1 818 324).

Appropriately, a combination of nonsharp and sharp (crystallizative) removal of the acrylic acid from the product gas mixture of the gas phase partial oxidation to be employed as described has at least one outlet for secondary components other than acrylic acid which boil at a higher temperature than acrylic acid under standard pressure (1 bar). Advantageously in application terms, this is on the side of the nonsharp separating processes. In general, the outlet of this type used will be the bottoms liquid of a separating column, from which separating column the liquid phase P (the crude acrylic acid to be used as such) itself or the stream to be converted later to the liquid phase P is withdrawn, for example, via a side draw and/or via a top draw. Of course, such an outlet may also be on the side of the inventive crystallizative removal. In this case, the outlet may consist of liquid residual phase R (mother liquor). Typically, there is additionally an outlet for secondary components which boil at a lower temperature than acrylic acid at standard pressure on the side of the nonsharp separating processes.

Advantageously, the acrylic acid present in the liquid phase P as the target product X is based on a partial oxidation product gas mixture which comprises:
1 to 30% by volume of acrylic acid,
$\geq 0$ to or 0.005 to 10% by volume of propylene,
$\geq 0$ or 0.001 to 2% by volume of acrolein,
$\geq 0$ or 0.001 to 2% by volume of methacrolein,
$\geq 0$ or 0.001 to 2% by volume of methacrylic acid,
$\geq 0$ or 0.005 to 10% by volume of molecular oxygen,
$\geq 0$ or 0.005 to 3% by volume of acetic acid,
$\geq 0$ or 0.001 to 2% by volume of propionic acid,
$\geq 0$ or 0.001 to 2% by volume of formaldehyde,
$\geq 0$ or 0.001 to 2% by volume of other aldehydes,
and 10 to 98 or 50 to 98% by volume of (inert) diluent gases.

The diluent gases may, for example, comprise:
$\geq 0$ or 0.005 to 90% by volume of saturated $C_1$-$C_6$-hydrocarbons (especially propane, methane and/or ethane),
$\geq 0$ or 0.05 to 30% by volume of steam,
$\geq 0$ or 0.05 to 15% by volume of carbon oxides (CO and/or $CO_2$),
and $\geq 0$ or 1 to 90% by volume of molecular nitrogen.

The partial oxidation product gas mixture may be derived especially from a partial oxidation as described in documents EP-A 1 818 324, DE-A 10 2004 032 129 and their equivalent foreign patents, DE-A 102 45 585, WO 03/076370, WO 01/96271, EP-A 117 146, WO 03/011804, U.S. Pat. No. 3,161,670, DE-A 33 13 573, DE-A 103 16 039 and WO 01/96270, proceeding from propylene and/or propane, and, as a propylene source, may have a propane dehydrogenation and/or oxydehydrogenation (if appropriate under heterogeneous catalysis) as a preceding reaction stage.

Advantageously, the crude acrylic acid desired to obtain the liquid phase P to be treated in accordance with the invention will be obtained from the aforementioned product gas mixtures of the $C_3$ acrylic acid precursor partial oxidation by condensing the acrylic acid out of the product gas mixture of the partial oxidation. The condensate obtained, as such or after additional addition of constituents $B_i$ to establish the desired $M_B^{tot}$, advantageously forms the liquid phase P to be treated in accordance with the invention in one of the two operating states I, II. Advantageously, the acrylic acid is condensed out of the product gas mixture (which has been cooled beforehand if appropriate) as a fractional condensation (on which is additionally superimposed, if appropriate, an absorption with water and/or aqueous solution, in order to reduce acrylic acid losses; cf., for example, EP-A 1 818 324), as described in detail, for example, in documents EP-A 1 015 410, WO 2004/035514, DE-A 102 43 625, EP-A 1 015 411, DE-A 102 35 847, German application 102007004960.0, EP-A 1 159 249, EP-A 1 163 201, EP-A 1 066 239 and EP-A 920 408.

In this case, the product gas mixture is appropriately, if appropriate on completion of direct and/or indirect cooling (for example with a quench liquid according to EP-A 1 066 239, or according to EP-A 1 163 201), fractionally condensed in a separating column having separating internals, ascending into itself, with side draw removal of crude acrylic acid (which as such may form the liquid phase P to be treated in accordance with the invention; if appropriate, the crude acrylic acid is treated by rectification and/or distillation or admixed with constituents $B_i$ to obtain the liquid phase P).

Fine acrylic acid crystals can then be removed in accordance with the invention from liquid phase P obtained by condensation in this way (and if appropriate additionally by rectification and also if appropriate after additions of constituents $B_i$ (preferably acid water)). Mother liquor (residual phase R) removed subsequently from the suspension S obtainable will, according to the model, for example, of EP-A 920 408 or WO 2004/035514, be recycled at least partly, preferably completely, into the condensation of the acrylic acid out of the product gas mixture. The high boiler outlet will be sited below the side draw of the crude acrylic acid.

Liquid phase P (crude acrylic acid) which has been obtained in this way by partial or total condensation and/or superimposed absorption with water or aqueous solution (comprises generally $\geq 90\%$ by weight, frequently $\geq 95\%$ by weight, of water; cf. EP-A 1 818 324) and if appropriate rectificative aftertreatment and if appropriate addition of constituents $B_i$ (e.g. acid water) and is to be treated in accordance with the invention may comprise:
$\geq 85$ to 99.5% by weight of acrylic acid,
$\geq 0$, generally 0.1 to 40% by weight of water,
$\geq 0$, generally 0.001 to 5% by weight of acrolein,
$\geq 0$, in some cases 0.001 to 10% by weight of methacrolein,
$\geq 0$, in some cases 0.001 to 10% by weight of methacrylic acid,
$\geq 0$, generally 0.01 to 10 or to 5% by weight of acetic acid,
$\geq 0$, generally 0.01 to 5% by weight of propionic acid,
$\geq 0$, generally 0.001 to 5% by weight of formaldehyde,
$\geq 0$, generally 0.001 to 5% by weight of aldehydes other than formaldehyde (per aldehyde),
$\geq 0$, generally 0.01 to 5% by weight of maleic acid,
$\geq 0$, generally 0.01 to 10% by weight of benzaldehyde and/or benzoic acid, and
$\geq 0$ to 3% by weight of protoanemonin.

For the separation of suspension S into crystals present therein and liquid residual phase R (mother liquor), a process according to the invention is quite generally followed by all processes detailed in documents WO 01/77856, WO 02/055469 and WO 03/078378 for separating suspension crystals and mother liquor (for example mechanical separating processes such as centrifugation). Preference is given to separation in a wash column. Advantageously, this is a wash column with forced transport of the deposited crystals (e.g. acrylic acid crystals). The proportion by volume of crystals in the crystal bed generally reaches values of >0.5. In general, the wash column is operated at values of from 0.6 to 0.75. The wash liquid used is advantageously the melt of crystals (e.g. acrylic acid crystals) purified (removed) beforehand in the wash column. The wash is normally effected in countercurrent. The process according to the invention thus especially comprises processes which comprise the following process steps (these processes are also employable in this way in the case of target products other than acrylic acid):

a) (in both operating states I, II) inventive crystallizative removal of acrylic acid (as the target product) from a liquid phase P (for example from liquid crude acrylic acid) with formation (withdrawal) of a suspension S,
b) separation of the suspension S into acrylic acid crystals and mother liquor (liquid residual phase R),
c) at least partial melting of the acrylic acid crystals removed and
d) at least partial recycling of the molten acrylic acid crystals to step b) and/or to step a).

Step b) is preferably effected by countercurrent washing with molten acrylic acid crystals removed beforehand recycled in step b). Advantageously, steps b), c) and d) are effected in a wash column.

In other words, the process according to the invention also comprises processes in which the liquid phase P comprising acrylic acid as the target product is converted in accordance with the invention to a suspension S consisting of acrylic acid crystals and liquid residual phase R (mother liquor), a portion of the remaining mother liquor (liquid residual phase R) is, if appropriate, removed mechanically from the suspension S, and the acrylic acid crystals are freed of remaining mother liquor in a wash column, with the proviso that a) the liquid phase P in both operating states I, II, based on the acrylic acid present therein, comprises from 0.20 to 30, frequently to 20, often to 10% by weight of water, and
b) the wash liquid used is the melt of acrylic acid crystals purified in (removed in a purifying manner from) the wash column.

In particular, the process according to the invention comprises the above processes, wherein the liquid phase P comprises $\geq 70\%$ by weight, or $\geq 75\%$ by weight, or $\geq 80\%$ by weight, or $\geq 85\%$ by weight, or $\geq 90\%$ by weight, or $\geq 95\%$ by weight, of acrylic acid.

Moreover, it is advantageous in accordance with the invention when the water content of the liquid phase P comprising acrylic acid as the target product X in the above-described procedures (or quite generally when the process according to the invention is employed), based on acrylic acid present in the liquid phase P, at least in operating state II, is from 0.2 or 0.4 to 8, or to 10, or to 20, or to 30% by weight, or from 0.60 to 5% by weight, or from 0.60 to 3% by weight.

Of course, the process according to the invention can also be applied to all crude acrylic acids of WO 98/01414, and to all crude p-xylenes of EP-A 097405, as the liquid phase P.

In general, the temperature of the crystal suspension S when withdrawn from the secondary chamber ($T_S^{out}$), in the case of use of crude acrylic acid as the liquid phase P comprising the target product X in the process according to the invention, in both operating states I, II, is in the range from $-25°$ C. to $+14°$ C., especially in the range from $-5°$ C. to $+12°$ C. and particularly advantageously in the range from 4 or 6 to 9° C.

All of the aforementioned is true in particular when the wash column is a wash column with forced transport of the acrylic acid crystals, and in particular when it is a hydraulic or mechanical wash column according to WO 01/77056 and is operated as stated there.

All of the aforementioned is true in particular when the wash column is configured and is operated according to the teachings of German application 10 2007 004 960.0, WO 03/041832 and of WO 03/041833 and WO 2006/111565.

The process according to the invention thus permits, with the sequence of "partial oxidation of at least one $C_3$ precursor compound, fractional acrylic acid condensation from the product gas mixture of the partial oxidation, inventive crystallizative removal of acrylic acid from the acrylic acid condensate withdrawn as the liquid phase P from the acrylic acid condensation (if appropriate after addition of constituents $B_i$ to adjust $M_B^{tot}$) while conducting an acrylic acid crystal suspension S out of the secondary chamber of the heat transferrer, and separating the suspension S into remaining mother liquor and pure acrylic acid crystals in a wash column using a melt of pure acrylic acid crystals removed beforehand as the wash liquid", in a highly efficient manner, the preparation of superabsorbent-grade acrylic acid adjusted to the particular market demand.

Of course, all process steps in which acrylic acid is involved are performed with inhibition of polymerization. The procedure may be as described in the prior art. A prominent position among the entirety of the available acrylic acid process stabilizers is taken by dibenzo-1,4-thiazine (PTZ), 4-hydroxy-2,2,6,6-tetramethylpiperidine 1-oxyl (4-OH-TEMPO) and p-methoxyphenol (MEHQ), which may each be part of the liquid phase P (for example of the crude acrylic acid) alone, in pairs or as a three-substance mixture. Typically, their total amount based on acrylic acid present in the liquid phase P is from 0.001 to 2% by weight.

In a corresponding manner to that outlined in an illustrative manner for acrylic acid, the process according to the invention can also be integrated into the preparation process of other target products X.

In other words, the present application comprises, in particular, a process in which the process according to the invention is followed by a process for continuously removing the fine crystals of the target product X present in the suspension S, in which the suspension S is fed to a wash column which has a wash column wall which surrounds a process chamber,
mother liquor (liquid residual phase R) is released from the process chamber while retaining the crystals present in the suspension S to form a crystal bed in the process chamber from the suspension S conducted into the process chamber by means of filter equipment,
the crystal bed is conveyed within the process chamber,
at least one force other than gravity acts in the process chamber in the conveying direction of the crystal bed and conveys the crystal bed within the process chamber,
pure melt which consists of molten crystals which have been removed beforehand by this wash column separating process is conducted within the process chamber in countercurrent to the crystal bed such that a wash front which divides the crystal bed into a mother liquor zone and into a pure melt zone forms in the crystal bed, and
crystals in the wash column washed in solid and/or molten form are discharged continuously at the opposite end of the wash column to the feed of the suspension S.

The aforementioned is true in particular when the target product X in the process according to the invention is acrylic acid (especially when the liquid phase P in at least one of the two operating states I, II is crude acrylic acid according to this document). In general, in this case, the removal of the fine acrylic acid crystals is followed by a further process in which acrylic acid crystals removed are melted and then subjected to a polymerization (preferably a free-radical polymerization) with themselves or with other at least monoethylenically unsaturated compounds (for example to a solution polymerization, emulsion polymerization, suspension polymerization, gas phase polymerization, or bulk polymerization). Such a process may also follow when the separation of crystals and mother liquor (liquid residual phase R) is undertaken in a different manner than with a wash column.

The aforementioned wash column is advantageously a hydraulic wash column or a mechanical wash column. Descriptions of corresponding wash columns can be found, for example, in WO 2006/111565, in DE-A 10 2007 032 633, in WO 03/041832, in WO 03/041833, in DE-A 10 2005 015 639 and in WO 01/77056, and the prior art cited in these documents.

To establish the desired degree of crystallization Y of the suspension S conducted out of the secondary chamber of the heat transferrer, it is possible in the process according to the invention to employ, for example, the difference between the crystallization heat flow $\dot{Q}_{Kr,Y}$ which evolves theoretically in the secondary chamber according to the degree of crystallization Y, calculated at the particular operating time with the aid of a process computer, and the difference formed between the total heat flow $\dot{Q}_{out}$ otherwise conducted out of the secondary chamber of the heat transferrer and the total heat flow $\dot{Q}_{in}$ otherwise conducted into the secondary chamber of the heat transferrer. The control parameter used may, appropriately in application terms, be $T_K^{in}$.

For the performance of the process according to the invention, all kinds of indirect heat transferrers (by definition they have the primary chamber/secondary chamber structure required in accordance with the invention) are useful in principle (cf., for example, Kristallisation, Grundlage und Technik [Crystallization, Fundamentals and Technology], Günther Metz, Springer-Verlag, Berlin 1969, p. 214 ff., and Ullmanns Encyclopädie der technischen Chemie, Verfahrenstechnik I [Process Technology I], Verlag Chemie Weinheim, 4th edition, 1972, page 672-682, and the prior art mentioned in these standard works).

Preferably in accordance with the invention, the indirect heat transferrer used is one in which the side of the at least one dividing wall dividing the at least one primary chamber from the secondary chamber in each case which faces the secondary chamber is operated with wiping (continuous scratching of the relevant heat-transferring area with the aid of suitable wiping apparatus). Such indirect heat transferrers (crystallizers, coolers) are frequently also referred to as scraped-surface coolers. The at least one primary chamber may be introduced in the indirect heat transferrer either so as to be immobile or so as to be mobile (for example removable cooling disks). In the latter case, the movable primary chamber elements can be exchanged from time to time.

The conveying motion of the fluid phase present in the secondary chamber through said chamber is in many cases already sufficient to cause suspension of the crystals removed in the secondary chamber. In general, however, the secondary chamber additionally has one or more mixing devices. In the simplest case, this may be sparging with an auxiliary gas (e.g. air), one or more stirrers, the wiping apparatus and/or pumped circulation. The conveying of the mass flow fed to the secondary chamber through said space is normally accomplished by forcing liquid phase P into the secondary chamber with the aid of pumps. The removal of (crystal) suspension S from the secondary chamber is effected typically under overflow control (but it can also be effected under level control through an immersed tube).

For this purpose, advantageously in application terms, a height-adjustable overflow weir is used.

As an illustrative selection, the following can be used for the process according to the invention:
  rotary tube crystallizers (the secondary chamber is the tube interior; the tube shell is a jacket within which the coolant is conducted in cocurrent or in countercurrent to the mass flow inside the tube; the tube interior is preferably slightly tilted from the horizontal; any crystal crusts forming on the tube interior can continuously be knocked off (for example with chains) and/or scratched off (with radial wipers); the liquid phase P is fed continuously into one end of the tube; the suspension S is conducted out continuously at the other end of the tube);
  a vessel with hung cooling elements (cooling elements (e.g. cooling disks) are hung in an unstirred vessel; the liquid phase P is, for example, conducted into the vessel bottom left, and the suspension S is conducted out of the vessel under overflow control top right; any cooling elements having encrustations are replaced by fresh cooling elements);
  stirred vessels (these are, for example, vessels which are surrounded by a cooling jacket and/or equipped with cooling elements (cooling coils, cooling disks); in addition, they have a stirrer which mixes the contents of the interior not occupied by the cooling elements continuously by stirring; the liquid phase P is fed in by pumps and the suspension S is conducted out by overflow);
  votator (jacket-cooled tube at rest, whose wall is scraped by flat scratching blades pressed on with springs; the liquid phase P is pumped in at one end, the suspension S flows out at the other end);
  pan crystallizer (trough-like vessel with horizontal shaft on which are mounted, at regular intervals, hollow pans (hollow disks) which are flowed through by the cooling medium generally in countercurrent to the crystallizing liquid phase P and which have sector-shaped cutouts for the passage of liquid phase P or crystal suspension; gentle passage of the crystal suspension through the pans and the coolant lines connecting them; the liquid phase P is conducted into the pan crystallizer on one side by pumps and conducted out of the pan crystallizer under overflow control on the opposite side);
  forced-circulation crystallizer from Swenson or Messo Chemietechnik.

Crystallizers particularly suitable for the process according to the invention (especially in the case of acrylic acid, methacrylic acid, p-xylene or N-vinylpyrrolidone as target product X) are cooling disk crystallizers (cooling disks present in the secondary chamber comprise the primary chambers), for example those described in Research Disclosure Database Number 496005 (published in August 2005) and in Research Disclosure Database Number 479008 (published in March 2004).

The fluid coolants (or assistants) used may be either gases or liquids. Preference is given in accordance with the invention to using liquid coolants (or heating media). Useful such liquid coolants (or heating media) include, for example, heat carrier oils, water, solutions of salts in water, mono- or polyhydric organic alcohols such as methanol, ethanol, propanol, glycol and/or glycerol, but also mixtures of one or more of the aforementioned coolants, for example water/methanol mixtures or water/glycol mixtures (for example with from 10 to 60% by weight of glycol).

The temperature $T_K^{in}$ in an inventive cooling crystallization is typically set from 0 to 20 K, often from 1 to 15 K and usually from 2 to 10 K below $T_S^{out}$ (that temperature with which the suspension S is withdrawn from the secondary chamber).

In many cases, however, there remain dividing wall area elements which can be wiped only with difficulty, if at all. This is, for example, the case when the primary chamber is the interior of a circular cooling disk which, for example, is immersed in a simple manner into the liquid phase flowing in the secondary chamber. While the front side and the back side of the cooling disk are amenable to wiping in a comparatively simple manner, this is normally not the case for the outer area of the cooling disk. Such area elements are therefore generally subjected to trace heating, which is intended to suppress their encrustation with crystals. Such trace heating may, for example, be resistance trace heating. It will be appreciated that such trace heating can also be implemented by indirect heat exchange.

For example, in the case of use of the circular cooling disks addressed above, it is possible to mount, on their outer area (to the unwiped disk wall end side), for example, a hollow heating tube (or another hollow profile), into which a fluid heating medium is supplied continuously with the temperature $T_H^{in}$ and out of which the same fluid heating medium is conducted again with the temperature $T_H^{out} < T_H^{in}$. The fluid heating medium is preferably likewise a liquid. More preferably, the heating medium is the same substance which is conducted through the primary chamber simultaneously as a coolant with another temperature. The temperature $T_H^{in}$ is appropriately selected within a range above $T_S^{out}$, for example in the range from 0 to 20 K, often from 0.5 to 10 K and usually from 1 to 5 K higher.

The constituents $B_i$ in the present invention are normally molecular compounds. In the case that they are ionic or strongly polar compounds, the degree of dissociation of these compounds in the liquid phase P may also have to be taken into account in a known manner for the number of moles $n_i$ relevant in accordance with the invention.

The crystals in the crystal suspension which form in the course of performance of the process according to the invention typically have a longitudinal dimension (longest direct straight line connecting two points on the crystal surface) in the range from 1 to 10 000 μm, often from 10 to 1000 μm, frequently from 100 to 800 μm and in many cases from 300 to 600 μm.

Otherwise, the crystallizative removal can be carried out like the suspension crystallizations performed in the prior art.

The (crystal) suspension S conducted out of an inventive removal is normally not fed directly to its separation of crystals and residual phase R (mother liquor). Instead, it is stored intermediately in a tank which is, for example, stirred and/or pumped in circulation and withdrawn continuously therefrom and fed, for example, to a wash column removal. When a plurality of (for example two or three) crystallizers (heat transferrers), for example of identical design, are operated in parallel in the inventive manner, all suspensions S (which essentially all have the same degree of crystallization Y) conducted in each case out of the different crystallizers, appropriately in application terms, are first fed to a buffer tank I and mixed therein by stirring. From this buffer tank I, the separating apparatuses for the mother liquor/crystal separation are then charged (for example hydraulic wash columns whose number advantageously corresponds to that of the crystallizers operated in parallel (but it may also be less or greater than this) and which are likewise operated in parallel (and are typically likewise of the same design)). The molten pure product withdrawn, for example, from the melt circuit of the particular wash column is fed to a common storage tank in which the arriving pure product streams are mixed with one another. From the storage tank, the pure target product X (polymerization-inhibited if appropriate) can then be sent to the particular consumer. From the mother liquor (liquid residual phase R) removed, frequently at least a portion is recycled into a nonsharp separating process employed to prepare the liquid phase P (cf. FIG. 5 of WO 01/77056 or German application 10 2007 004 960.0). This recycling is generally not effected directly out of the apparatus used to separate mother liquor and crystals.

Instead, the mother liquor removed (the liquid residual phase R removed) is first fed to a common buffer vessel II, in which the residual phases R fed in from the different separating apparatuses (for example wash columns) are mixed with one another. Any overflow from the buffer tank I comprising the suspension S is also fed to this buffer vessel II. The recycling into an aforementioned nonsharp separating process can then be effected from this buffer vessel II (for example in the case of acrylic acid as the target product X, according to FIG. 5 of WO 01/77056 or according to the teaching of German application 10 2007 004 960.0, into the fractional condensation of the product gas mixture of the heterogeneously catalyzed partial gas phase oxidation of a $C_3$ precursor compound of acrylic acid). When, in the course of such an acrylic acid preparation, there is, for example, a requirement for warm rinsing acrylic acid in order, for example, to rinse filters encrusted with crystals to free them of the crystals in the hydraulic wash column used to separate crystals and liquid residual phase, this is appropriately likewise withdrawn from the buffer vessel II.

An increase of $\dot{m}_X$ is possible in a simple manner in the process according to the invention by increasing the (mass) flow of liquid phase P comprising target product X fed to the secondary chamber (the flow of this feed stream is increased). For this purpose, the space-time yield is normally increased in existing production plants for preparing the liquid phase P. In the case of a heterogeneously catalyzed partial gas phase oxidation to prepare target product X (e.g. acrylic acid or methacrylic acid), this is possible, for example, in a simple manner by increasing the loading of the fixed catalyst bed with reaction gas mixture and the loading of the apparatuses downstream of the partial oxidation for removing the target product X from the product gas mixture of the partial oxidation with product gas mixture (cf., for example, DE-A 103 37 788 and the prior art cited in this document).

The working pressures typically employed for the process according to the invention are normally not more than 5 bar, usually not more than 3 bar, frequently not more than 2 bar and generally $\leq 1.5$ bar and $\geq 1$ bar. For reasons of, for example, monomer removal by suction, the working pressure may also be below atmospheric pressure. The present invention thus comprises especially the following embodiments:

1. A process for operating a continuous removal of a target product X in the form of fine crystals of the target product X from a liquid phase P which consists of the target product X and of constituents $B_i$ other than the target product X and whose total mole fraction of constituents $B_i$ has the value $M_B^{tot}$, with the aid of an indirect heat transferrer which has a secondary chamber and at least one primary chamber, in which the secondary chamber and the at least one primary chamber are each separated spatially from one another by at least one material dividing wall which serves as a surface for transfer of heat out of the secondary chamber into the at least one primary chamber, in which a stream of liquid phase P and, as a constituent thereof, a mass flow $\dot{m}_X$ of target product X are conducted into the secondary chamber of the heat transferrer, while the at least one primary chamber is simultaneously flowed through by at least one fluid cooling medium which is fed to the at least one primary chamber with the temperature $T_K^{in}$ such that fine crystals of the target product X are formed from the liquid phase P in the secondary chamber to leave a liquid residual phase R and are suspended in the remaining liquid residual phase R which, compared to the liquid phase P, comprises the constituents other than the target product X in enriched form and whose content of target product X is at least 70% by weight, to obtain a suspension S having a degree of crystallization Y of fine crystals of the target product X in the liquid residual phase R, and a stream of the suspension S is conducted continuously out of the secondary chamber of the heat transferrer, in different operating states I and II, the at least one fluid cooling medium with the temperature $T_K^{in}$ (I) being fed to the at least one primary chamber and the stream of liquid phase P with a mass flow $\dot{m}_X$(I) of target product X present in the same stream being fed to the secondary chamber in the operating state I, and the at least one fluid cooling medium with the temperature $T_K^{in}$ (II) being fed to the at least one primary chamber and the stream of liquid phase P with a mass flow $\dot{m}_X$(II) of target product X present in the same stream being fed to the secondary chamber in operating state II, with the proviso that $\dot{m}_X$(II)>$\dot{m}_X$(I) and $T_K^{in}$(II)<$T_K^{in}$(I),
wherein the total mole fraction $M_B^{tot}$ of constituents $B_i$ other than the target product X in the liquid phase P fed to the secondary chamber is greater in operating state II than in operating state I.
2. The process according to embodiment 1, wherein the degree of crystallization Y in operating state I and in operating state II is from 0.10 to 0.50.
3. The process according to embodiment 1, wherein the degree of crystallization Y in operating state I and in operating state II is from 0.20 to 0.40.
4. The process according to embodiment 1, wherein the degree of crystallization Y in operating state I and in operating state II is from 0.25 to 0.35.
5. The process according to any of embodiments 1 to 4, wherein the difference between $\dot{m}_X$(I) and $\dot{m}_X$(II), based on the arithmetic mean of $\dot{m}_X$(I) and $\dot{m}_X$(II), is at least 5%.
6. The process according to any of embodiments 1 to 4, wherein the difference between $\dot{m}_X$(I) and $\dot{m}_X$(II), based on the arithmetic mean of $\dot{m}_X$(I) and $\dot{m}_X$(II), is at least 20%.
7. The process according to any of embodiments 1 to 4, wherein the difference between $\dot{m}_X$(I) and $\dot{m}_X$(II), based on the arithmetic mean of $\dot{m}_X$(I) and $\dot{m}_X$(II), is at least 50%.
8. The process according to any of embodiments 1 to 7, wherein the degree of crystallization Y in operating state I, Y (I), and the degree of crystallization Y in operating state II, Y (II), based on the arithmetic mean of Y (I) and Y (II), differ from one another by not more than 20%.
9. The process according to any of embodiments 1 to 8, wherein the difference between $T_K^{in}$ (II) and $T_K^{in}$ (I) is from 0.1 to 30 K.
10. The process according to any of embodiments 1 to 8, wherein the difference between $T_K^{in}$ (II) and $T_K^{in}$ (I) is at least 0.3 K.
11. The process according to any of embodiments 1 to 8, wherein the difference between $T_K^{in}$ (II) and $T_K^{in}$ (I) is at least 0.5 K.
12. The process according to any of embodiments 1 to 11, wherein the content in the liquid residual phase present in the suspension S withdrawn from the secondary chamber of target product X in the two operating states I, II is $\geq 80\%$ by weight.
13. The process according to any of embodiments 1 to 11, wherein the content in the liquid residual phase present in the suspension S withdrawn from the secondary chamber of target product X in the two operating states I, II is $\geq 90\%$ by weight.
14. The process according to any of embodiments 1 to 13, wherein the target product X is acrylic acid, methacrylic acid, p-xylene or N-vinylpyrrolidone.
15. The process according to any of embodiments 1 to 14, wherein the total number of moles of constituents $B_i$ whose molecular weight is less than three times the molecular weight of the target product X present in the liquid phase P fed to the secondary chamber divided by the total number of moles of all constituents present in the same liquid phase P in operating state II is greater than the total number of moles of constituents $B_i$ whose molecular weight is less than three times the molecular weight of the target product X present in the liquid phase P fed to the secondary chamber divided by the total number of moles of all constituents present in the same liquid phase P in operating state I.
16. The process according to any of embodiments 1 to 14, wherein the total number of moles of constituents $B_i$ whose molecular weight is less than twice the molecular weight of the target product X present in the liquid phase P fed to the secondary chamber divided by the total number of moles of all constituents present in the same liquid phase P in operating state II is greater than the total number of moles of constituents $B_i$ whose molecular weight is less than twice the molecular weight of the target product X present in the liquid phase P fed to the secondary chamber divided by the total number of moles of all constituents present in the same liquid phase P in operating state I.
17. The process according to any of embodiments 1 to 14, wherein the total number of moles of constituents $B_i$ whose molecular weight is less than the molecular weight of the target product X present in the liquid phase P fed to the secondary chamber divided by the total number of moles of all constituents present in the same liquid phase P in operating state II is greater than the total number of moles of constituents $B_i$ whose molecular weight is less than the molecular weight of the target product X present in the liquid phase P fed to the secondary chamber divided by the total number of moles of all constituents present in the same liquid phase P in operating state I.
18. The process according to any of embodiments 1 to 14, wherein the mole fraction of $H_2O$ present in the liquid phase P fed to the secondary chamber in operating state II is greater than the mole fraction of $H_2O$ present in the liquid phase P fed to the secondary chamber in operating state I.
19. The process according to any of embodiments 1 to 18, wherein the target product X is acrylic acid which is derived from an acrylic acid preparation process which comprises a process for heterogeneously catalyzed partial gas phase oxidation of a $C_3$ precursor compound to a product gas mixture comprising acrylic acid and a subsequent removal of the acrylic acid from this product gas mixture, and $M_B^{tot}$ in the liquid phase P fed to the secondary chamber in operating state II is adjusted by using acrylic acid-comprising aqueous solution which has been withdrawn from the acrylic acid preparation process and whose water content is at least 60% by weight.
20. The process according to any of embodiments 1 to 19, wherein the target product X is acrylic acid which is derived from an acrylic acid preparation process which comprises a process for heterogeneously catalyzed partial gas phase oxidation of a $C_3$ precursor compound to a product gas mixture comprising acrylic acid and a subsequent removal of the acrylic acid from this product gas mixture, and $M_B^{tot}$ in the liquid phase P fed to the secondary chamber in operating state I is adjusted by using acrylic acid-comprising aqueous solution which has been withdrawn from the acrylic acid preparation process and whose water content is at least 80% by weight.

21. The process according to any of embodiments 1 to 20, wherein the target product X is acrylic acid which is derived from an acrylic acid preparation process which comprises a process for heterogeneously catalyzed partial gas phase oxidation of a $C_3$ precursor compound to a product gas mixture comprising acrylic acid, and a removal of acrylic acid from this product gas mixture by fractional condensation and/or absorption.

22. The process according to embodiment 21, which is followed by a process for separating the suspension S into crystals of the target product X present therein and liquid residual phase R present therein, and at least a portion of the liquid residual phase R is recycled into the fractional condensation and/or absorption.

23. The process according to any of embodiments 1 to 22, wherein the target product X is acrylic acid and the liquid phase P, in both operating states I, II, has the following contents:
    >70% by weight of acrylic acid,
    up to 15% by weight of acetic acid,
    up to 5% by weight of propionic acid,
    up to 5% by weight of low molecular weight aldehydes,
    up to 3% by weight of polymerization inhibitors,
    0 to 5% by weight of diacrylic acid, and up to 20% by weight of water.

24. The process according to any of embodiments 1 to 23, wherein operating state I is before operating state II in time and, at the transition from operating state I to operating state II, the increase from $M_B^{tot}$ (I) to $M_B^{tot}$ (II) is effected before the increase from $\dot{m}_X$(I) to $\dot{m}_X$(II).

25. The process according to any of embodiments 1 to 23, wherein operating state II is before operating state I in time and, at the transition from operating state II to operating state I, the lowering of $\dot{m}_X$(II) to $\dot{m}_X$(I) is effected before the lowering of $M_B^{tot}$(II) to $M_B^{tot}$(I).

26. The process according to any of embodiments 1 to 25, which, in addition to the process step according to embodiment 1, comprises the following process steps:
    b) separating the suspension S conducted out of the secondary chamber of the heat transferrer into crystals of the target product X and liquid residual phase R,
    c) at least partly melting the crystals of the target product X removed and
    d) at least partly recycling the molten crystals of the target product X to step b) and/or to the process step for continuous removal of the target product X according to embodiment 1.

27. The process according to any of embodiments 1 to 26, wherein the heat transferrer is a cooling disk crystallizer.

28. The process according to any of embodiments 1 to 27, wherein the heat transferrer is a scraped-surface cooler.

29. The process according to any of embodiments 1 to 28, which is followed by a process for continuously removing the fine crystals of target product X present in the suspension S, in which
    the suspension S is fed to a wash column which has a wash column wall which encloses a process chamber,
    while retaining the crystals present in the suspension S and while forming a crystal bed in the process chamber from the suspension S conducted into the process chamber, liquid residual phase R is released from the process chamber through filter devices,
    the crystal bed is conveyed within the process chamber,
    in the process chamber, at least one force other than gravity acts in the conveying direction of the crystal bed and conveys the crystal bed within the process chamber,
    in the process chamber, in countercurrent to the crystal bed, pure melt consisting of molten crystals and crystals removed beforehand by this wash column process is conducted so as to form, in the crystal bed, a wash front which divides the crystal bed into a mother liquor zone and into a pure melt zone, and
    at the opposite end of the wash column to the feed of the suspension S, crystals washed continuously in the wash column are discharged in solid and/or molten form.

30. The process according to embodiment 29, wherein the target product X is acrylic acid, and the process is followed by a further process in which removed and molten acrylic acid crystals are subjected to a polymerization with themselves or with other at least monoethylenically unsaturated compounds.

31. A process for preparing a target product X, which includes a process according to any of embodiments 1 to 29.

EXAMPLE AND COMPARATIVE EXAMPLE

I. Two identical stirred and wiped cooling disk crystallizers of the design described in Research Disclosure Database Number 496005 (published in August 2005) were operated in parallel. These were each a trough in which 24 wiped circular cooling plates (cooling disks) at an equidistant interval of 30±1 cm were arranged hung in succession. The plate diameter was 3.3 m. The plate thickness was 5.2 cm. The coolant used for each of the two crystallizers was a mixture of 70% by weight of water and 30% by weight of glycol. The coolant was conducted through the crystallizer in countercurrent to the liquid phase P fed to the crystallizer in the particular crystallizer, and passed on from cooling disk to the next cooling disk but one. In other words, the coolant in each of the two crystallizers was conducted in the form of two equal and parallel streams through the cooling plates of the particular crystallizer. Half of the stream led through the numerically even cooling plates; the other half of the stream led through the numerically odd cooling plates (numbering of the cooling disks in flow direction of the coolant beginning with 1). The coolant areas were manufactured from stainless steel (DIN material 1.4541). The wall thickness of the stainless steel cooling areas was 4 mm. The rotation speed of the wipers was from 5 to 6 revolutions per minute. The shaft conducted through the center of the cooling disks, which drives the wipers, was sealed with water-flushed stuffing box packings (packing threads made of Teflon; flush rate equals a few liters per hour up to a few 10 s of l/h per seal). On the circumference of each cooling disk, where it is not possible to wipe, a hollow profile was mounted (a tube welded on; (material: stainless steel (DIN material 1.4541), wall thickness 3.6 mm)). For the purpose of trace heating the individual cooling disks of a crystallizer, a liquid heating medium flowed in to the hollow profile thereof, which was likewise composed of 70% by weight of water and 30% by weight of glycol.

The wipers were segmented in the radial direction (4 segments).

The specific pressing force of the wipers in the installed state at right angles to the cooling surface was about 4 N per cm of active wiping edge length. The wiper material used was Multilene® PE 1000. In addition to the wipers, the shaft drove paddles (between two cooling disks and before the first and last cooling disk, in each case in symmetrical arrangement), which brought about improved mixing. In the rear part of the particular crystallizer in conveying direction of the crystal suspension (beyond the last cooling disk), the (crystal) suspension S formed in the individual crystallizer in each case flowed over an overflow weir into a buffer tank stirred with a helical stirrer (made of stainless steel of DIN materials No. 1.4541 or 1.4571), from which two identical hydraulic melt wash columns were charged in parallel with suspension S withdrawn from the buffer tank (separation of the mass flow of suspension S withdrawn from the buffer tank between the two wash columns was followed in each case, before entry into the particular wash column, by flow through a coriolis mass flow meter for the purpose of determining the degree of crystallization Y via the mass density of the particular partial mass flow) for the purpose of separating it into residual phase R and crystals. The separation in the melt wash columns was effected as described in documents EP-A 1 272 453, EP-A 1448283, WO 2006/111565, WO 03/041833, EP-A 1 305 097, DE-A 101 56 016, DE-A 10 2005 018702, DE-A 102 23 058 and German application 10 2007 004 960.0. The internal diameter of the individual wash column was 1.4 m. The wash columns were charged with crystal suspension S in each case by means of a centrifugal pump (Kanalrad type), and the flow was controlled by means of speed regulation of the pumps. The liquid residual phase R removed in the wash columns was recycled via a buffer vessel, as described in FIG. 5 of WO 01/77056 or in German application 10 2007 004 960.0, into the fractional condensation also used to prepare the liquid phase P comprising acrylic acid as the target product.

The steady-state contents in the buffer tank of crystal suspension S were 16 m$^3$.

Each of the two crystallizers had a roof (stainless steel (DIN material 1.4541)) and was sealed against ingress of ambient air. Both the wash columns, which were likewise manufactured from stainless steel (DIN material 1.4541, wall thickness 10 mm) and the crystallizers and the buffer tank were thermally insulated and provided with a steam barrier (cf., for example, DE-A 10 2007 032 633) by means of Alu-Butyl foil from WeGo Systembaustoffe, VTI branch in 67014 Ludwigshafen/Rhein adhesive-bonded to Styropor applied to their stainless steel shell.

The wash columns, the buffer tank and the crystallizers were accommodated in a common housing. The air temperature in the overall housing was between 25° C. and 28° C. The mass transfer from the crystallizers into the buffer tank and from there into the wash column was effected likewise sealed from the ambient air, and also with heat insulation and water vapor sealing. The degree of crystallization Y was set independently to 0.28 for each of the two crystallizers operated in parallel. A closed-loop control deviation was counteracted in both cases by increasing or lowering the particular $T_K^{in}$.

The starting state was an operating state I of the two crystallizers, which was characterized by the following boundary conditions:

Target product X=acrylic acid.

Phase P (I) fed to the crystallizers=crude acrylic acid which derived from a fractional condensation of a product gas mixture of a two-stage heterogeneously catalyzed partial gas phase oxidation of chemical grade propylene to acrylic acid. Its content of acrylic acid was 94.44% by weight. $M_B^{tot}$ (I) was 0.1483.

The entrance temperature of the coolant into the primary chamber region of the particular crystallizer $T_K^{in}$ (I) was approx. 2.1° C.

The exit temperature of the coolant from the primary chamber region of the particular crystallizer $T_K^{out}$ (I) was approx. 4.7° C.

The coolant mass flow $\dot{m}_K$ (I) fed to the primary chamber of the particular crystallizer was approx. 208 t/h.

The entrance temperature of the heating medium into the particular hollow profile of the cooling disks of the particular crystallizer $T_H^{in}$ (I) was approx. 12° C.

The exit temperature of the heating medium from the particular hollow profile of the cooling disks of the particular crystallizer $T_H^{out}$ (I) was approx. 10.4° C.

The total heating medium mass flow $\dot{m}_H$ (I) fed to the hollow profiles of the cooling disks of the particular crystallizer was approx. 43 t/h.

The entrance temperature of liquid phase P (I) into the particular secondary chamber, $T_P^{in}$ (I), was approx. 14° C.

The temperature of the suspension S (I) on withdrawal from the particular secondary chamber $T_S^{out}$ (I) was approx. 7.0° C.

The acrylic acid content of the liquid residual phase R in the suspension S (I) withdrawn from the secondary chamber was 92.34% by weight.

The mass flow $\dot{m}_P$ (I) with which the liquid phase P (I) was fed to the secondary chamber of the particular crystallizer and the suspension S was conducted out of the secondary chamber of the particular crystallizer was approx. 26.4 t/h. This gave rise to an $\dot{m}_X$ (I) of approx. 24.9 t/h for each secondary chamber.

The wipers were able, in operating state I, to keep the surfaces of the cooling disks of the particular cooling disk crystallizer free of crystals without any trouble over an operating time of 15 h.

II. In the operating state (II), an increased mass flow $\dot{m}_P$ (II) was fed to the secondary chamber of the particular crystallizer.

By addition of acid water withdrawn from the fractional condensation (it comprised 10.8% by weight of acrylic acid, 79.5% by weight of water, 6.4% by weight of acetic acid and 2.47% by weight of formaldehyde) to the liquid phase P, $M_B^{tot}$ was increased in operating state II to the value of $M_B^{tot}$ (II)=0.1724. The acrylic acid content of the liquid phase P (II) was thus 93.73% by weight.

The mass flow $\dot{m}_P$ (II) with which the liquid phase P (II) was fed to the secondary chamber of the particular crystallizer was approx. 33 t/h. This gave rise to an $\dot{m}_X$ (II) of approx. 31 t/h for each secondary chamber.

In order to maintain the degree of crystallization Y of the suspension S withdrawn from the particular secondary chamber of 0.28, $T_K^{in}$ had to be lowered to the value of $T_K^{in}$ (II) of approx. −0.3° C. with an otherwise unchanged cooling mode in the two crystallizers. $T_K^{out}$ (II) was approx. 3.0° C. The trace heating was maintained unchanged with a $T_H^{in}$(II) of approx. 12° C. $T_H^{out}$(II) was approx. 10° C. The acrylic acid content of the liquid residual phase R in the suspension S (II) withdrawn from the secondary chamber was approx. 91.34% by weight.

The wipers were able, in operating state II, to keep the surfaces of the cooling disks of the particular cooling disk crystallizer free of crystals without any trouble over an operating time of 15 h.

III. In the comparative operating state (C), a mass flow $\dot{m}_P$ (C) of approx. 32.5 t/h of essentially the same liquid phase P as in operating state I was fed to the secondary chamber of the particular crystallizer. $\dot{m}_X$(C) was thus approx. 30.7 t/h for each secondary chamber.

In order to maintain the degree of crystallization Y of the suspension S withdrawn from the particular secondary chamber of 0.28, $T_K^{in}$ had to be adjusted to the value $T_K^{in}$ (C) of approx. 0.6° C. with an otherwise unchanged cooling mode in the two crystallizers. $T_K^{out}$ (C) was approx. 3.8° C. The trace heating was maintained unchanged with a $T_H^{in}$ (C) of 12° C. $T_H^{out}$ (C) was approx. 10° C. The acrylic acid content of the liquid residual phase R in the suspension S(C) withdrawn from the secondary chamber was 92.3% by weight.

After an operating time of 15 h in the comparative operating state (C), several cooling disks of the two crystallizers were covered with a persistent crystal encrustation of about 1-2 cm in thickness, which had not been removed by the wipers.

U.S. Provisional Patent Application No. 60/972,023, filed Sep. 13, 2007, is incorporated into the present application by literature reference.

With regard to the abovementioned teachings, numerous changes and deviations from the present invention are possible. It can therefore be assumed that the invention, within the scope of the appended claims, can also be performed differently than the way described specifically herein.

The invention claimed is:

1. A process for operating a (A) continuous removal of a target product X in the form of crystals of the target product X from a liquid phase P which consists of the target product X and of constituents $B_i$ other than the target product X and whose total mole fraction of the constituents $B_i$ has a value $M_B^{tot}$, the process comprising:
   (a1) conducting a stream of the liquid phase P and, as a constituent thereof, a mass flow $\dot{m}_X$ of the target product X into a secondary chamber of an indirect heat transferrer comprising the secondary chamber and at least one primary chamber, in which the secondary chamber and the at least one primary chamber are each separated spatially from one another by at least one material dividing wall which serves as a surface for transfer of heat out of the secondary chamber into the at least one primary chamber;
   (a2) simultaneously flowing at least one fluid cooling medium through the at least one primary chamber wherein the at least one fluid cooling medium is fed to the at least one primary chamber with a temperature $T_K^{in}$, such that the crystals of the target product X are formed from the liquid phase P in the secondary chamber to form a suspension S comprising the crystals of the target product X and a liquid residual phase R in which the crystals of the target product X are suspended, said liquid residual phase R, compared to the liquid phase P, comprising the constituents other than the target product X in enriched form and having a content of the target product X of at least 70% by weight, and said suspension S having a degree of crystallization Y of the crystals of the target product X in the liquid residual phase R; and
   (a3) continuously conducting a stream of the suspension S out of the secondary chamber of the heat transferrer, wherein the heat transferrer cools the suspension S under different operating states I and II:
      (I) the at least one fluid cooling medium with a temperature $T_K^{in}$(I) is fed to the at least one primary chamber, and the stream of liquid phase P with a mass flow $\dot{m}_X$ (II) of the target product X is fed to the secondary chamber, and
      (II) the at least one fluid cooling medium with a temperature $T_K^{in}$ (II) is fed to the at least one primary chamber, and the stream of liquid phase P with a mass flow $\dot{m}_X$ (II) of the target product X is fed to the secondary chamber,
   with the proviso that $\dot{m}_X$(II)>$\dot{m}_X$(I) and $T_K^{in}$ (II)<$T_K^{in}$ (I),
   wherein a total mole fraction $M_B^{tot}$ of the constituents $B_i$ other than the target product X in the liquid phase P fed to the secondary chamber is greater in operating state II than in operating state I, and
   wherein the target product X is acrylic acid, methacrylic acid, p-xylene, or N-vinvlpyrrolidone.

2. The process according to claim 1, wherein the degree of crystallization Y in the operating state I and in the operating state II is from 0.10 to 0.50.

3. The process according to claim 1, wherein the degree of crystallization Y in the operating state I and in the operating state II is from 0.20 to 0.40.

4. The process according to claim 1, wherein the degree of crystallization Y in the operating state I and in the operating state II is from 0.25 to 0.35.

5. The process according to any of claims 1 to 4, wherein a difference between $\dot{m}_X$(I) and $\dot{m}_X$(II), based on an arithmetic mean of the $\dot{m}_X$(I) and the $\dot{m}_X$(II), is at least 5%.

6. The process according to any of claims 1 to 4, wherein a difference between the $\dot{m}_X$(I) and the $\dot{m}_X$(II), based on an arithmetic mean of the $\dot{m}_X$(I) and the $\dot{m}_X$(II), is at least 20%.

7. The process according to any of claims 1 to 4, wherein a difference between the $\dot{m}_X$(I) and the $\dot{m}_X$(II), based on an arithmetic mean of the $\dot{m}_X$(I) and the $\dot{m}_X$(II), is at least 50%.

8. The process according to claim 1, wherein the degree of crystallization Y in the operating state I, Y (I), and the degree of crystallization Y in the operating state II, Y (II), based on an arithmetic mean of the Y (I) and the Y (II), differ from one another by not more than 20%.

9. The process according to claim 1, wherein a difference between the $T_K^{in}$ (II) and the $T_K^{in}$ (I) is from 0.1 to 30 K.

10. The process according to claim 1, wherein a difference between the $T_K^{in}$ (II) and the $T_K^{in}$ (I) is at least 0.3 K.

11. The process according to claim 1, wherein a difference between the $T_K^{in}$ (II) and the $T_K^{in}$ (I) is at least 0.5 K.

12. The process according to claim 1, wherein a content in the liquid residual phase, present in the suspension S withdrawn from the secondary chamber, of the target product X in the two operating states I, II is $\geq$80% by weight.

13. The process according to claim 1, wherein a content in the liquid residual phase, present in the suspension S withdrawn from the secondary chamber, of the target product X in the two operating states I, II is $\geq$90% by weight.

14. The process according to claim 1, wherein a total number of moles of the constituents $B_i$ whose molecular weight is less than three times a molecular weight of the target product X present in the liquid phase P divided by a total number of moles of all constituents present in the same liquid phase P in the operating state II is greater than the total number of moles of the constituents $B_i$ whose molecular weight is less than three times the molecular weight of the target product X present in the liquid phase P divided by total number of moles of all constituents present in the same liquid phase P in the operating state I.

15. The process according to claim 1, wherein a total number of moles of the constituents $B_i$ whose molecular weight is less than twice a molecular weight of the target product X present in the liquid phase P divided by the total number of moles of all constituents present in the same liquid phase P in the operating state II is greater than the total number of moles of the constituents $B_i$ whose molecular weight is less than twice the molecular weight of the target product X present in the liquid phase P divided by a total number of moles of all constituents present in the same liquid phase P in the operating state I.

16. The process according to claim 1, wherein a total number of moles of the constituents $B_i$ whose molecular weight is less than a molecular weight of the target product X present in the liquid phase P fed to the secondary chamber divided by a total number of moles of all constituents present in the same liquid phase P in the operating state II is greater than the total number of moles of the constituents $B_1$ whose molecular weight is less than the molecular weight of the target product X present in the liquid phase P fed to the secondary chamber divided by a total number of moles of all constituents present in the same liquid phase P in the operating state I.

17. The process according to claim 1, wherein a mol fraction of $H_2O$ present in the liquid phase P fed to the secondary chamber in the operating state II is greater than a mol fraction of $H_2O$ present in the liquid phase P fed to the secondary chamber in the operating state I.

18. The process according to claim 1, wherein
the target product X is acrylic acid obtained from an acrylic acid preparation process comprising:
oxidizing, in a heterogeneously catalyzed partial gas phase oxidation, a $C_3$ precursor compound to a product gas mixture comprising acrylic acid; and
subsequently removing of the acrylic acid from the product gas mixture, and
$M_B^{tot}$ in the liquid phase P fed to the secondary chamber in the operating state II is adjusted with an acrylic acid-comprising aqueous solution which has been withdrawn from the acrylic acid preparation process and whose water content is at least 60% by weight.

19. The process according to claim 1, wherein
the target product X is acrylic acid obtained from an acrylic acid preparation process comprising:
oxidizing, in a heterogeneously catalyzed partial gas phase oxidation, a $C_3$ precursor compound to a product gas mixture comprising acrylic acid; and
subsequently removing the acrylic acid from the product gas mixture, and
$M_B^{tot}$ in the liquid phase P fed to the secondary chamber in the operating state I is adjusted with an acrylic acid-comprising aqueous solution which has been withdrawn from the acrylic acid preparation process and whose water content is at least 80% by weight.

20. The process according to claim 1, wherein
the target product X is acrylic acid obtained from an acrylic acid preparation process comprising:
oxidizing, in a heterogeneously catalyzed partial gas phase oxidation, a $C_3$ precursor compound to a product gas mixture comprising acrylic acid; and
removing acrylic acid from the product gas mixture by fractional condensation and/or absorption.

21. The process according to claim 20, further comprising, subsequently:
separating the suspension S into crystals of the target product X present in the suspension and the liquid residual phase R present in the suspension, and at least a portion of the liquid residual phase R is recycled into the fractional condensation and/or absorption.

22. The process according to claim 1, wherein the target product X is acrylic acid and the liquid phase P, in both operating states I, II, comprises:

>70% by weight of acrylic acid,
up to 15% by weight of acetic acid,
up to 5% by weight of propionic acid,
up to 5% by weight of low molecular weight aldehydes,
up to 3% by weight of polymerization inhibitors,
0 to 5% by weight of diacrylic acid, and
up to 20% by weight of water.

23. The process according to claim 1, wherein
(i) the operating state I is before the operating state II in time, and,
(ii) at a transition from the operating state I to the operating state II, an increase from $M_B^{tot}$ (I) to $M_B^{tot}$ (II) is effected before an increase from $\dot{m}_X$ (I) to $\dot{m}_X$ (II).

24. The process according to claim 1, wherein
(i) the operating state II is before the operating state I in time, and,
(ii) at a transition from the operating state II to the operating state I, a lowering of $\dot{m}_X$ (II) to $\dot{m}_X$ (I) is effected before a lowering of $M_B^{tot}$ (II) to $M_B^{tot}$ (I).

25. The process according to claim 1, further comprising:
b) separating the suspension S conducted out of the secondary chamber of the heat transferrer into crystals of the target product X and liquid residual phase R,
c) at least partly melting the crystals of the target product X removed and
d) at least partly recycling the molten crystals of the target product X to the separating b) and/or to (a1) of the continuous removal of the target product X.

26. The process according to claim 1, wherein the heat transferrer is a cooling disk crystallizer.

27. The process according to claim 1, wherein the heat transferrer is a scraped-surface cooler.

28. The process according to claim 1, which is followed by a second process for continuously removing the fine crystals of target product X present in the suspension S, said second process comprising:
feeding the suspension S to a wash column which has a wash column wall which encloses a process chamber,
while retaining the crystals present in the suspension S and while forming a crystal bed in the process chamber from the suspension S conducted into the process chamber,
releasing the liquid residual phase R from the process chamber through at least one filter device,
conveying the crystal bed within the process chamber,
in the process chamber, allowing at least one force other than gravity to act in the conveying direction of the crystal bed and convey the crystal bed within the process chamber,
in the process chamber, in countercurrent to the crystal bed, conducting a pure melt comprising molten crystals and crystals removed beforehand by this wash column process so as to form, in the crystal bed, a wash front which divides the crystal bed into a mother liquor zone and into a pure melt zone, and
at an opposite end of the wash column to the feed of the suspension S, discharging crystals washed continuously in the wash column in solid and/or molten form.

29. The process according to claim 28, wherein the target product X is acrylic acid, and the second process is followed by a third process comprising:
polymerizing removed and molten acrylic acid crystals with themselves or with at least one other at least monoethylenically unsaturated compound.

30. A process for preparing a target product X, which comprises the process according to claim 1.

* * * * *